(12) United States Patent
Higashi et al.

(10) Patent No.: US 8,390,816 B2
(45) Date of Patent: Mar. 5, 2013

(54) METHOD FOR ATTENUATED TOTAL REFLECTION FAR ULTRAVIOLET SPECTROSCOPY AND AN APPARATUS FOR MEASURING CONCENTRATIONS THEREWITH

(75) Inventors: Noboru Higashi, Neyagawa (JP);
Naomi Kariyama, Neyagawa (JP);
Akifumi Ikehata, Tsukuba (JP)

(73) Assignee: Kurashiki Boseki Kabushiki Kaisha, Kurashiki-shi (JP)

( * ) Notice: Subject to any disclaimer, the term of this patent is extended or adjusted under 35 U.S.C. 154(b) by 365 days.

(21) Appl. No.: 12/921,066

(22) PCT Filed: Mar. 3, 2009

(86) PCT No.: PCT/JP2009/053957
§ 371 (c)(1),
(2), (4) Date: Sep. 3, 2010

(87) PCT Pub. No.: WO2009/110463
PCT Pub. Date: Sep. 11, 2009

(65) Prior Publication Data
US 2011/0013193 A1    Jan. 20, 2011

(30) Foreign Application Priority Data
Mar. 4, 2008 (JP) .................................. 2008-053527

(51) Int. Cl.
*G01N 21/47* (2006.01)
*G01N 21/55* (2006.01)

(52) U.S. Cl. ........................... 356/446; 356/445

(58) Field of Classification Search .......... 356/445–448, 356/450–458
See application file for complete search history.

(56) References Cited

U.S. PATENT DOCUMENTS 3,975,084 A * 8/1976 Block ............................. 356/335
5,097,130 A * 3/1992 Koashi et al. ............. 250/339.09
(Continued)

FOREIGN PATENT DOCUMENTS

EP    1 998 163 A1    12/2008
JP    7-12713 A    1/1995
(Continued)

OTHER PUBLICATIONS

Higashi, N. et al., "Potential of Far-Ultraviolet Absorption Spectroscopy as a Highly Sensitive Quantitative and Qualitative Analysis Method for Aqueous Solutions, Part I: Determination of Hydrogen Chloride in Aqueous Solutions", vol. 58, No. 8, 2004. pp. 910-916.

(Continued)

*Primary Examiner* — Gregory J Toatley
*Assistant Examiner* — Jarreas C. Underwood
(74) *Attorney, Agent, or Firm* — Birch, Stewart, Kolasch & Birch, LLP

(57) ABSTRACT

In far ultraviolet spectroscopy using attenuated total reflection, total reflection light is measured by using evanescent waves of total reflection light. The penetration depth thereof is equal to or larger than 150 nm in a wavelength range in the far ultraviolet range wherein the penetration depth depends on a wavelength of the far ultraviolet light, refractive index of an object to be measured, refractive index of optical material of the probe and incident angle of the far ultraviolet light at an interface between the probe and the object. The attenuated total reflection probe is made of an optical material selected so as to have the penetration depth equal to or higher than 150 nm in far ultraviolet wavelength range, and the probe makes contact with the object to be measured at the interface, and the far ultraviolet light is incident on the interface at incident angle larger than critical angle in the wavelength range so as to have the penetration depth equal to or higher than 150 nm. The total reflection light from the interface is measured, and absorbance of the object to be measured is determined.

13 Claims, 8 Drawing Sheets

U.S. PATENT DOCUMENTS

| | | | |
|---|---|---|---|
| 7,791,729 B2* | 9/2010 | Higashi et al. | 356/445 |
| 7,823,215 B2* | 10/2010 | Giakos | 850/31 |
| 7,978,331 B2* | 7/2011 | Higashi et al. | 356/445 |
| 2009/0073436 A1 | 3/2009 | Higashi et al. | |

FOREIGN PATENT DOCUMENTS

| | | |
|---|---|---|
| JP | 8-75639 A | 3/1996 |
| JP | 10-82738 A | 3/1998 |
| JP | 2003-512615 A | 4/2003 |
| JP | 2004-157031 A | 6/2004 |
| JP | 2005-214863 A | 8/2005 |
| JP | 2005-233884 A | 9/2005 |
| JP | 2006-23200 A | 1/2006 |
| JP | 2006-234663 A | 9/2006 |
| JP | 2007-155494 A | 6/2007 |
| JP | 2007-279025 A | 10/2007 |
| WO | WO 01/29537 A2 | 4/2001 |
| WO | WO 2006/109408 A1 | 10/2006 |
| WO | WO 2007/108328 A1 | 9/2007 |

OTHER PUBLICATIONS

Higashi, Noboru et al.,"An attenuated total reflectance far-UV spectrometer", Review of Scientific Instruments, vol. 78, 103107/1-103107/5, 2007, American Institute of Physics.

Ikehata, Akifumi et al., "Direct observation of the absorption bands of thefl first electronic transition in liquid H2O and D2O by attenuated total reflectance far-UV spectroscopy", The Journal of Chemical Physics, vol. 129, 234510/1-234510/5, 2008, American Institute of Physics.

International Search Report, dated Jun. 2, 2009 issued in PCT/JP2009/053957.

Mitsuoka, M. et al., "Analysis of Dissolved Ions of Very Low Concentration in an Aqueous Solution with ATR Far Ultraviolet Spectroscopy—Optimization of Penetration Depth", Presentation Summaries for the 56th Annual Meeting of the Japan Society for Analytical Chemistry, J2003, p. 226, Sep. 5, 2007.

* cited by examiner

METHOD FOR ATTENUATED TOTAL REFLECTION FAR ULTRAVIOLET SPECTROSCOPY AND AN APPARATUS FOR MEASURING CONCENTRATIONS THEREWITH

TECHNICAL FIELD

The invention relates to spectroscopic analysis using attenuated total reflection in the far ultraviolet range.

BACKGROUND ART

Recently, it is needed to measure very small concentrations in an aqueous solution in a semiconductor fabrication process or the like. For example, it is needed to measure and manage concentrations in an etching liquid or a cleaning liquid used in an etching process for a silicon wafer or the like precisely, simply and fast.

The inventors proposed a chemical analysis using far ultraviolet spectroscopy in order to analyze very small concentrations of solutes in an aqueous solution (JP-A 2005-214863, and Applied Spectroscopy Vol. 58 (2004)910-916). In the analysis, absorption of far ultraviolet light is measured in a slope (for example, 170 to 210 nm) in the higher wavelength side of a peak of an absorption band of water (due to n→σ* transition of water molecules) appearing in the far ultraviolet range. Because the absorption band is very sensitive to a change in hydrogen bonds of water molecules, a quantitative measurement can be performed on components hydrated in an aqueous solution with higher sensitivity than in near infrared and infrared spectroscopy. In some cases, absorption spectra of a water-soluble component itself also appear in the far ultraviolet range below 300 nm, and a plurality of soluble components can be analyzed with far ultraviolet spectroscopy in a wavelength range between 170 and 300 nm.

However, as the measurement wavelength of transmitting light becomes shorter further in the far ultraviolet range, optical absorption due to water becomes larger, and the transmittance becomes smaller. Therefore, a spectroscopic measurement becomes impossible if an optical cell with a very short optical path is not available. In order to solve this problem, the inventors focus attention to an attenuated total reflection optical probe (ATR probe). Light absorption due to attenuated total reflection is explained here. When a light ray entering a medium having a higher refractive index (such as synthetic quartz) is incident on an interface between the medium and another medium having a lower refractive index (for example, a sample to be measured such as water), the light ray is reflected totally if the incident angle is larger than the critical angle. However, the light ray penetrates into the other medium having a lower refractive index, by a certain distance of the order of wavelength, propagates in the direction of the interface, and is reflected. This penetrating light ray is called evanescent waves. The amplitude of electric field of the evanescent waves is highest at the reflection point, and it attenuates quickly in a direction perpendicular to the interface and along the interface. The distance at which the amplitude of electric field decreases to 1/e is called penetration depth. According to the attenuated total reflection spectroscopy, light is absorbed due to the penetration of the evanescent waves of the order of wavelength, and the light absorption can be detected in the reflected light. Because the penetration depth corresponds to optical path length in a conventional transmission spectra measurement, absorption spectra similar to that obtained with a very short optical path length can be realized theoretically.

It is to be noted that a material of an ATR probe is limited because it should have refractive index always higher than the sample and sufficient transmittance in the measurement wavelength range. Then, the inventors thought that a special type of ATR probe is necessary in order to measure the absorption band due to n→σ* transition in water in the far ultraviolet range because the above-mentioned conditions on the refractive index and transmittance have to be satisfied, and they proposed a special type of ATR probe (JP-A 2007-279025).

The invention can be applied to concentration measurement for a processing liquid used in a semiconductor process, and a prior art concentration measurement is explained here. As to a processing liquid of mixed acids used in silicon wafer cleaning process, photo-etching process and the like, a cleaning water having radical components such as hydroxyl radicals and the like, concentration management is necessary on viewpoints of yield, safety, working efficiency and the like, and concentration analysis is needed for the concentration management. Recently, various types of methods are proposed (for examples, JP-A 2007-155494, 2006-234663 and 7-12713). However, in these measurement methods, for example, a cleaning liquid overflowing from a processing vessel is sampled, or a liquid in a circulation line is sampled. Thus, they cannot be used to measure the concentration directly in real time. Recently, because etching and cleaning processes are controlled at higher precision, it is needed to monitor correct concentrations in a cleaning liquid in a processing vessel, and still further to measure concentration distribution in the processing liquid. In order to solve such a problem, a compact optical probe of immersion type is proposed (JP-A 2006-23200), and it can be used for an in-line measurement on temperature and solute concentrations at any point in a vessel. However, immersing a probe into a vessel has problems on an influence on circulation of cleaning liquid in the vessel, and on decrease in capacity for a wafer or wafers to be immersed.

SUMMARY OF THE INVENTION

An object of the invention is to perform far ultraviolet spectroscopy without using an ATR probe having a special structure.

Another object of the invention is to measure concentrations of components in real time in a cleaning liquid in a cleaning process in situ, without sampling the cleaning liquid.

In a method for measuring total reflection light with a probe for far ultraviolet attenuated total reflection spectroscopy according to the invention, penetration depth of evanescent waves of total reflection light is equal to or higher than 150 nm in a far ultraviolet wavelength range. The penetration depth is determined by wavelength of far ultraviolet light, refractive index of an object to be measured, refractive index of an optical material of the probe and incident angle of the far ultraviolet light entering an interface between the probe and the object. The attenuated total reflection probe is made of an optical material selected so as to have the penetration depth equal to or higher than 150 nm in a far ultraviolet wavelength range, and making the probe contact with the object to be measured at an interface therewith. The far ultraviolet light is incident on the interface, and the light has incident angle larger than critical angle in the wavelength range so as to have the penetration depth equal to or higher than 150 nm. The total reflection light from the interface is measured, and absorbance of the object to be measured is obtained.

A first apparatus according to the invention for measuring concentrations with attenuated total reflection far ultraviolet spectroscopy, includes an attenuated total reflection probe made of synthetic quartz, fixed to and integrated with a wall made of synthetic quartz of a cleaning vessel for containing a cleaning liquid for a semiconductor, a guiding optical system for guiding far ultraviolet light ray to an interface between the probe and the cleaning liquid at an incident angle larger than critical angle, and a receiving optical system for receiving total reflection light reflected from the interface with an optical detector.

A second apparatus according to the invention for measuring concentrations to be arranged beside a rotary stage on which a semiconductor is placed and to which a cleaning liquid for a semiconductor is ejected, includes an attenuated total reflection probe made of synthetic quartz, arranged at a position on which the cleaning liquid drops from the rotary stage, a guiding optical system for guiding far ultraviolet light ray generated by a light source to an interface between the probe and the cleaning liquid at an incident angle larger than critical angle, and a receiving optical system for receiving total reflection light reflected from the interface of the probe with an optical detector.

A third apparatus according to the invention for measuring concentrations to be integrated with a pipe though which a cleaning liquid for a semiconductor flows, the pipe being made of synthetic quartz, includes an attenuated total reflection probe made of synthetic quartz, fixed to and integrated with a wall made of synthetic quartz of a cleaning vessel for containing a cleaning liquid for cleaning a semiconductor, a guiding optical system for guiding far ultraviolet light ray generated by a light source to an interface between the probe and the cleaning liquid at an incident angle larger than critical angle, and a receiving optical system for receiving total reflection light reflected from the interface of the probe with an optical detector.

By optimizing the material of the ATR probe and the wavelength range of far ultraviolet light under a specified condition, concentrations of solutes in an aqueous solution can be measured very sensitively with the ATR far ultraviolet spectroscopy. Further, in a semiconductor fabrication process, the concentration of a cleaning liquid for a semiconductor can be measured sensitively in situ in a short time by using the ATR far ultraviolet spectroscopy.

EMBODIMENTS

Figure 1:
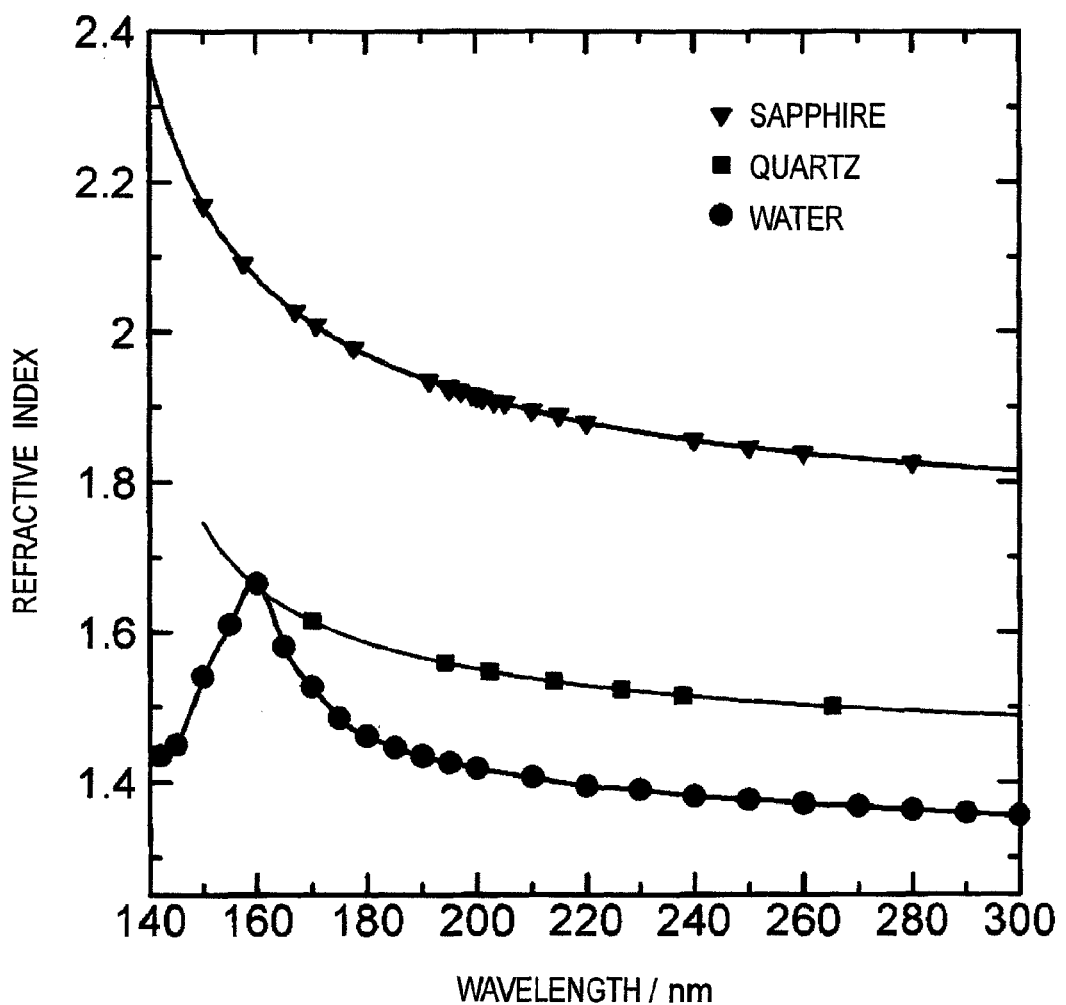
FIG. 1 is a graph of wavelength dependence of refractive indices of various optical materials in the far ultraviolet range.

Referring now to the drawings, embodiments of the invention are explained below.

As mentioned above, the inventors thought that a special type of ATR probe (prism) is necessary in order to measure the absorption band due to n→σ* transition of water in the far ultraviolet range because of the total reflection condition that the refractive index of the material of an ATR probe should be larger than that of the sample substance and the transmission condition that the transmittance of the material of the ATR probe should be sufficiently high in the measurement wavelength range. Then, they proposed a three-layer type ATR probe (JP-A 2007-279025). When refractive indices of sapphire and quartz as representative optical materials are compared, as shown in FIG. 1, sapphire has refractive index higher than water in the entire wavelength range. On the other hand, around 160 nm, quartz has refractive index lower than water, and total reflection does not occur. Thus, quartz cannot be used for an ATR probe.

However, when a far ultraviolet ATR probe is used to measure concentrations in a cleaning liquid in a vessel for cleaning a semiconductor, the material(s) of the ATR probe should not be soluble into a sample or should not be corroded by the sample. Further, it is also required that the material has refractive index always higher than water and that it has a sufficient transmittance. Therefore, the material to be used for an ATR probe is limited to high purity synthetic quartz, as mentioned above. Because synthetic quartz absorbs light strongly in infrared range, its usage is thought limited to a near infrared range. However, because the absorption of water is due to a forbidden transition in the near infrared range, the absorption is weak, and the measurement precision is not sufficient. Therefore, synthetic quartz has not yet been used for monitoring a cleaning liquid.

The inventors study a far ultraviolet ATR probe made of synthetic quartz in order to apply attenuated total reflection spectroscopy to a measurement of solute concentrations in a cleaning liquid used in a semiconductor cleaning process. They optimize penetration depth of total reflection light by selecting the incident angle condition and the measurement wavelength range of incident light by trial and error and succeed to measure optical absorption data. As a result, they propose a measurement method and a measurement apparatus, without using an ATR probe of a special structure mentioned above, for measuring very small concentrations of solutes in an aqueous solution. The measurement method and apparatus use an ATR probe made of an optical material having refractive index very close to that of an aqueous solution, and the penetration depth of evanescent waves of total reflection light is enlarged actively in order to measure optical absorption in the far ultraviolet range. This is explained below.

The penetration depth $d_p$ of evanescent waves at an interface of an ATR probe is calculated, as shown in a following formula, by using wavelength $\lambda$, incident angle $\theta$, refractive index $n_1$ of a probe material and refractive index $n_2$ of an object (water) to be measured.

$$d_p = \frac{\lambda}{2\pi n_1 \sqrt{\sin^2\theta - (n_2/n_1)^2}}$$

The total reflection occurs at incident angle $\theta$ equal to or larger than the critical angle.

$$\theta \geq \sin^{-1}(n_2/n_1)$$

Figure 2:
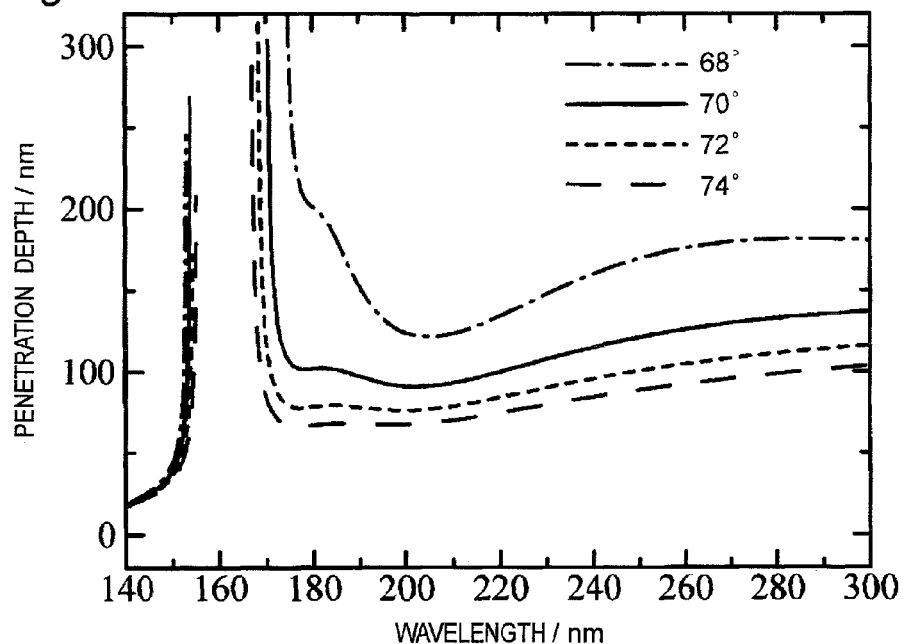
FIG. 2 is a graph of penetration depth of evanescent waves into water at a total reflection plane of a quartz probe.

FIG. 2 shows a result of calculation on a quartz probe of penetration depth into an object (water) to be measured. The data shows cases of incident angles θ of 68, 70, 72 and 74 degrees.

Because quartz has refractive index $n_2$ smaller than refractive index $n_1$ of water around 160 nm (refer to FIG. 1), if incident angle θ is 75 degrees or larger, light having a wavelength shorter than 168 nm cannot be reflected totally. Thus, the light transmits into water partially, and the absorbance of the sample cannot be measured. On the other hand, as shown in FIG. 2, at wavelengths around 170 nm, the penetration depth becomes large to a few hundreds nanometers or longer, so that the absorption band of water is observed at around 170 nm with use of the ATR measurement. Wavelengths around 170 nm correspond to a part of a slope of the absorption peak of water due to n→σ* transition. Because the absorbance of water depends on the concentrations of solutes in an aqueous solution, the ATR measurement can be used to analyze solute concentrations in an aqueous solution quantitatively. Previously, such an approach to use a wavelength range near a boundary of the total reflection condition actively has not been attempted in order to enhance and observe the far ultraviolet absorption spectra in the slope. However, the inventors find that the approach can be applied to quantitative analysis of solute concentrations in an aqueous solution, according to the above-mentioned optimization of the penetration depth by taking the total reflection condition into account. When an ATR probe is made of synthetic quartz used in order to measure an aqueous solution, the refractive index of water becomes close to that of synthetic quartz near the absorption peak of water. Therefore, the total reflection light is measured in a measurement wavelength range in the far ultraviolet range with the penetration depth of evanescent waves of total reflection light equal to or larger than 150 nm. Thus, the absorbance can be measured with high sensitivity. In this case, the measurement wavelength range is about 170 to 175 nm.

Further, even in a wavelength range of 175 to 300 nm wherein the refractive index of the object to be measured (water) is not so close to that of the optical material of the probe (synthetic quartz) in contrast to the wavelengths around 170 nm, the difference between the refractive indices is still small, and the penetration depth of the total reflection light is as large as about 100 nm. Therefore, the absorbance can be measured with the spectroscopic apparatus. Further, the absorption of a solute itself can also be measured in the wavelength range if any. The absorbance of an aqueous solution is very large in the far ultraviolet range between 170 and 300 nm, but sufficient measurement sensitivity can be obtained with the ATR measurement. Therefore, a measurement similar to the transmission measurement as described in JP-A 2005-214863 can be performed with an ATR probe on the total reflection light.

Figure 3:
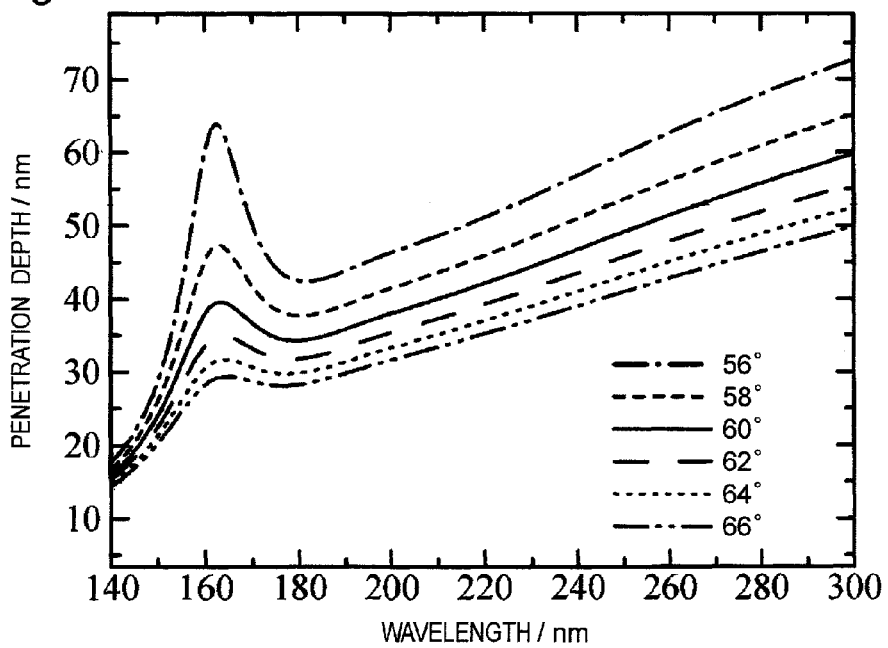
FIG. 3 is a graph of penetration depth of evanescent waves into water at a total reflection plane of a sapphire probe.

For comparison, FIG. 3 shows a calculation result on a sapphire probe of the penetration depth into water in cases of incident angles of 56 to 66 degrees. The penetration depth is 70 nm or smaller in the far ultraviolet range. In the case of sapphire probe, the ATR measurement is possible in the entire far ultraviolet wavelength range. However, because the difference of refractive index is large between the probe material and the object to be measured or water, and the penetration depth is smaller than 100 nm.

Figure 4:
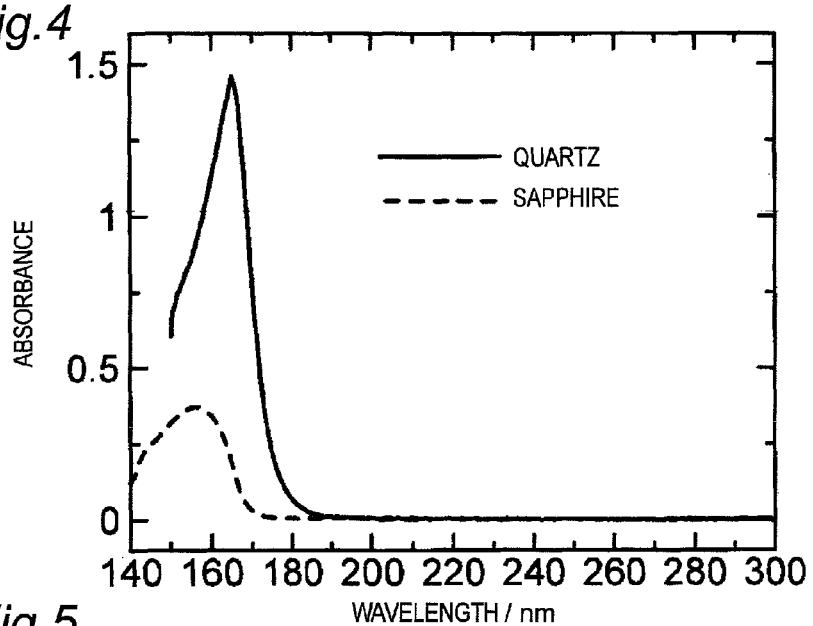
FIG. 4 is a graph of absorbance of water measured with a quartz ATR probe and with a sapphire ATR probe.

FIG. 4 shows absorbance of water measured with a quartz ATR probe and with a sapphire ATR probe. The absorption peak due to n→σ* transition of water is at around 150 nm inherently. If an ATR probe is made of an optical material such as sapphire having high refractive index, the absorption band of water is not observed at around 170 nm. On the contrary, if the optical material of an ATR probe is synthetic quartz, the penetration depth of evanescent waves becomes very large in a wavelength region where the refractive index of quartz becomes close to that of water. Then, the absorption band of water is observed in an enhanced magnitude at around 170 nm even in an ATR measurement.

Figure 5:
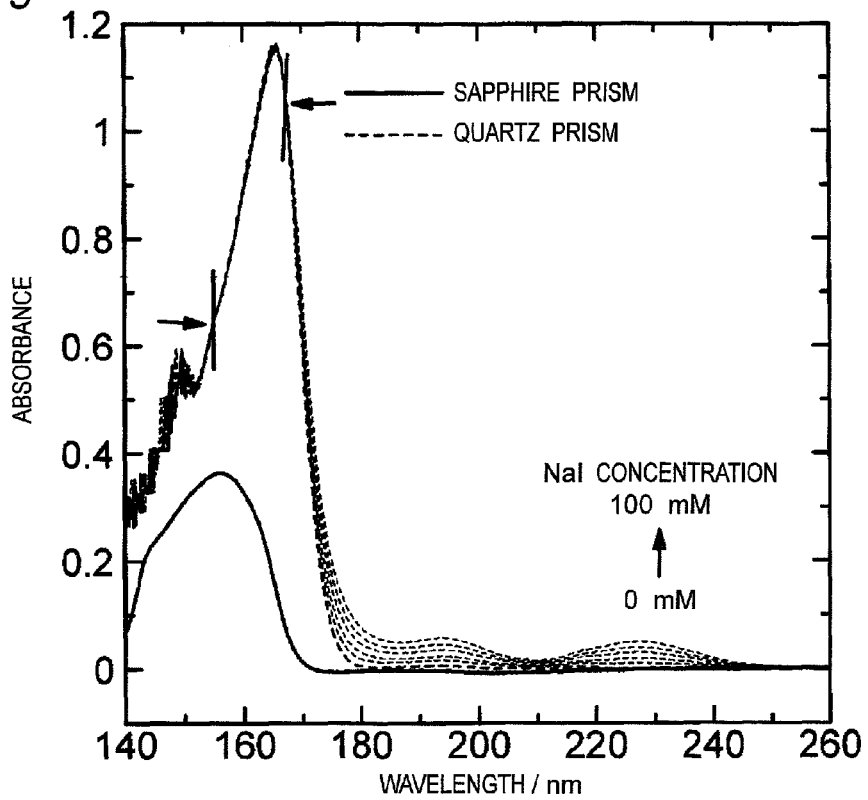
FIG. 5 is a graph of absorbance of NaI aqueous solutions measured with a quartz ATR probe and with a sapphire ATR probe.

FIG. 5 shows absorbance of sodium iodide (NaI) aqueous solutions in the far ultraviolet range, measured with a quartz probe and with a sapphire probe. It is to be noted that total reflection does not occur in a wavelength range indicated with two arrows. A peak around 230 nm is ascribed to the solute (NaI). NaI concentrations in the samples shown in FIG. 5 are 0, 20, 40, 60, 80 and 100 mM. As to the sapphire probe, data only on pure water is shown though the absorption due to NaI is also observed in the other samples, because the peak is low in the other samples.

Though measurements on aqueous solutions with an ATR probe made of quartz are explained above, a far ultraviolet spectroscopic measurement can be performed generally by enhancing the penetration depth of evanescent waves of total reflection light actively by using a probe made of a material having refractive index very close to that of a sample to be measured. The penetration depth of evanescent waves of total reflection light depends on wavelength of far ultraviolet light, refractive index of an optical material of the ATR probe, refractive index of a sample and an incident angle of ultraviolet light onto an interface between the probe and the sample. If an optical material having refractive index very similar to that of an object to be measured is available, the optical material, measurement wavelength and incident angle are selected so as to realize the penetration depth of 150 nm or larger into the sample to be measured. Then, the total reflection light from the interface is measured, and the absorbance of the sample is determined.

Figure 6:
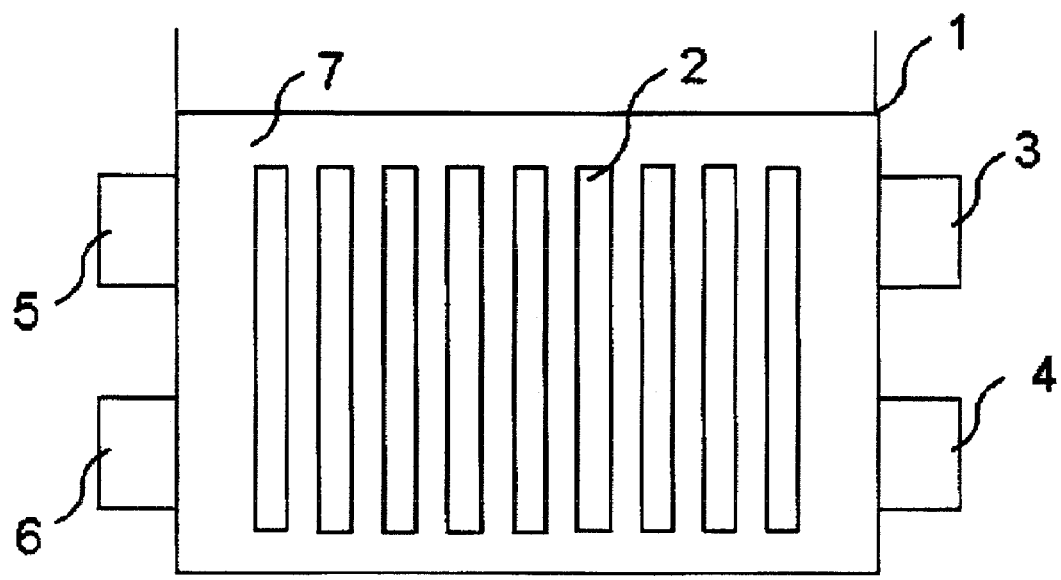
FIG. 6 is a diagram of a semiconductor cleaning system used in a batch cleaning process.

The measurement method explained above can be applied to management of component concentrations in a cleaning liquid and quality of water in a semiconductor cleaning system. FIG. 6 shows a cleaning vessel 1 used in a batch cleaning process. The cleaning vessel 1 is made of synthetic quartz, and it contains a chemical liquid 7. Wafers 2 are set in the cleaning vessel 1 and are immersed into the cleaning liquid. For example, four concentration measurement devices 3, 4, 5 and 6 are mounted on side faces of the cleaning vessel 1. A measurement device including an ATR probe can be set anywhere on the wall of the vessel 1. Thus, the concentration of the cleaning liquid can be checked in real time without taking out the cleaning liquid from the vessel 1. By providing a plurality of concentration measurement devices, variations of the concentration distribution in the cleaning liquid can be checked.

Figure 7:
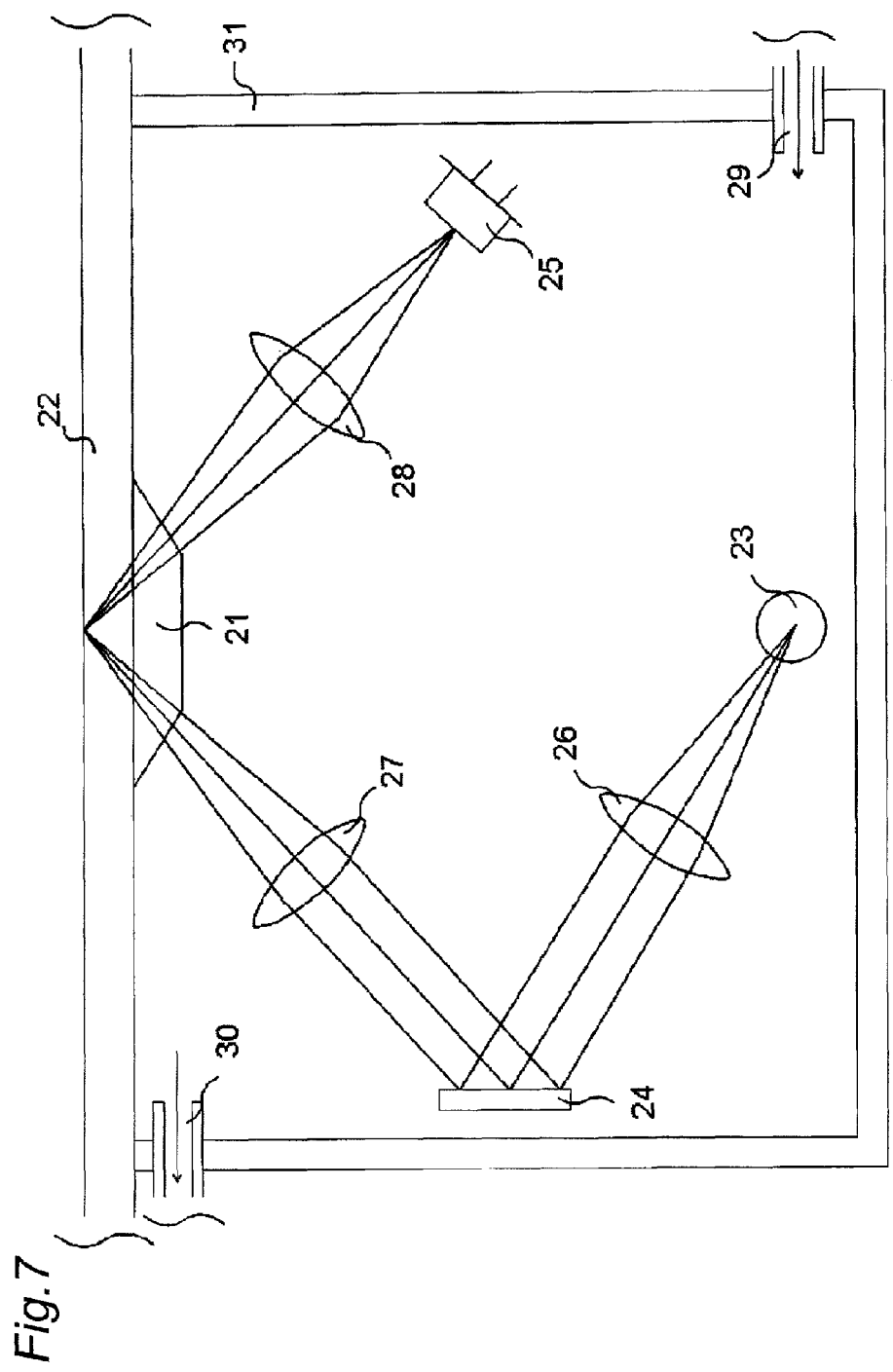
FIG. 7 is a diagram of an optical measurement portion provided in a concentration measurement apparatus.

FIG. 7 shows an optical measurement portion provided in the concentration measuring devices 3, 4, 5 and 6. An ATR probe 21 made of synthetic quartz, similarly to the wall 22 of the vessel, is fixed directly to the wall 22, or it is integrated with the wall 22. Light generated by an ultraviolet light source 23 such as a deuteron lamp is collimated by a projection lens 26, is reflected by a grating 24 as a monochromatic spectroscope, transmits a projection lens 27, and enters the ATR probe 21. These components form a guiding optical system for light propagating to the ATR probe 21. The incident angle of the light to the probe is set appropriately. Total reflection light from the ATR probe 21 transmits a lens 28 and enters an optical detector 25 such as an ultraviolet sensor. These components form a receiving optical system for receiving the total reflection light from the ATR probe 21 with the optical detector 25. Further, an airtight structure or housing 31 is provided to seal the optical systems in order to replace air with nitrogen gas around the in-coming and out-going faces of the ATR probe and the optical systems. In the airtight structure, nitrogen gas which does not absorb light in the far ultraviolet range is introduced through an inlet 29 and is discharged from an outlet 30. Thus, oxygen gas is purged from the optical systems. (Alternatively, argon gas may be used to replace air, or air itself may be evacuated.) Spectra measured with the optical detector 25 is processed by an external signal processor (not shown), and the absorbance is calculated based on the measurement data. A calibration curve can be created with a known multi-variante analysis on the absorbance at a plurality of wavelengths. By using the calibration curve, a measurement can be performed in real time. Thus, a concentration in a cleaning liquid in the cleaning vessel 22 can be measured directly. Because the ATR probe is made of synthetic quartz, similarly to the side face of the vessel, it can be prevented that impurities in the ATR probe 21 dissolve into the cleaning liquid or that the ATR probe itself is corroded by the cleaning liquid. Because only a small quantity of sample makes contact with the interface of the probe on which the ultraviolet light is incident, a change in sample quality due to ultraviolet exposure can be prevented.

Figure 8:
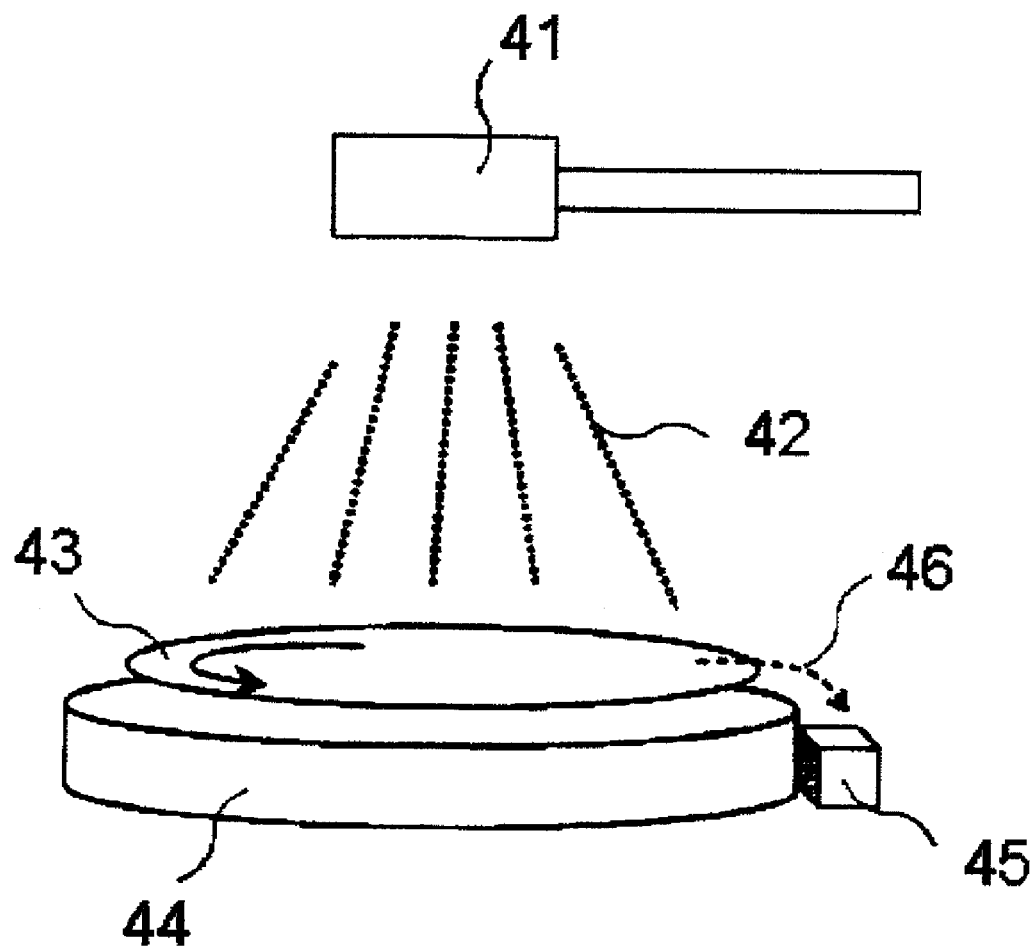
FIG. 8 is a diagram of an apparatus for measuring component concentrations in a cleaning liquid in a sheet-feed type semiconductor cleaning system.

FIG. 8 shows an apparatus for measuring concentrations of components in a cleaning liquid in a sheet-feed type semiconductor cleaning system. In the system, an ATR probe is fixed beside a rotary stage (or rotary stand) for a silicon wafer, and a cleaning liquid ejected onto the wafer drops onto the ATR probe. In detail, a nozzle 41 is positioned above the rotary stage 44, and it ejects (sprays) the cleaning liquid 42 onto a wafer 43 placed on the rotary stage 44. Cleaning liquid 46 after ejected onto the rotating wafer 43 drops externally in radial directions under centrifugal force due to the rotation of the rotary stage 44. A concentration measurement device 45 similar to that shown in FIG. 7 is set at a side of the rotary stage 44, and an ATR probe is positioned in the device 45 so that the interface with the cleaning liquid faces above. Thus, the absorbance of cleaning liquid dropped from the rotary stage 44 onto the ATR probe is measured.

Figure 9:
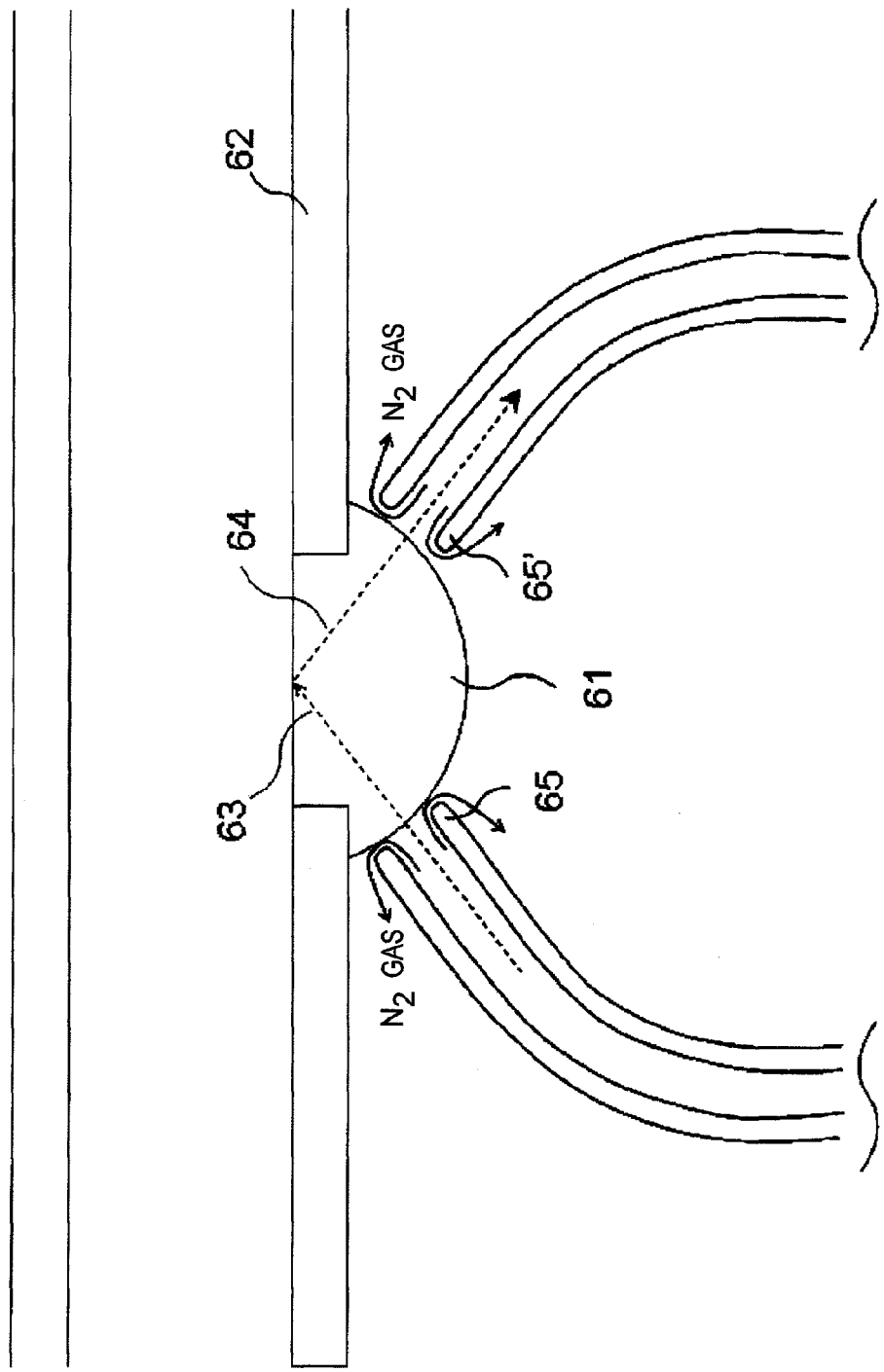
FIG. 9 is a diagram of a part of an optical system using hollow optical fibers.
Figure 10:
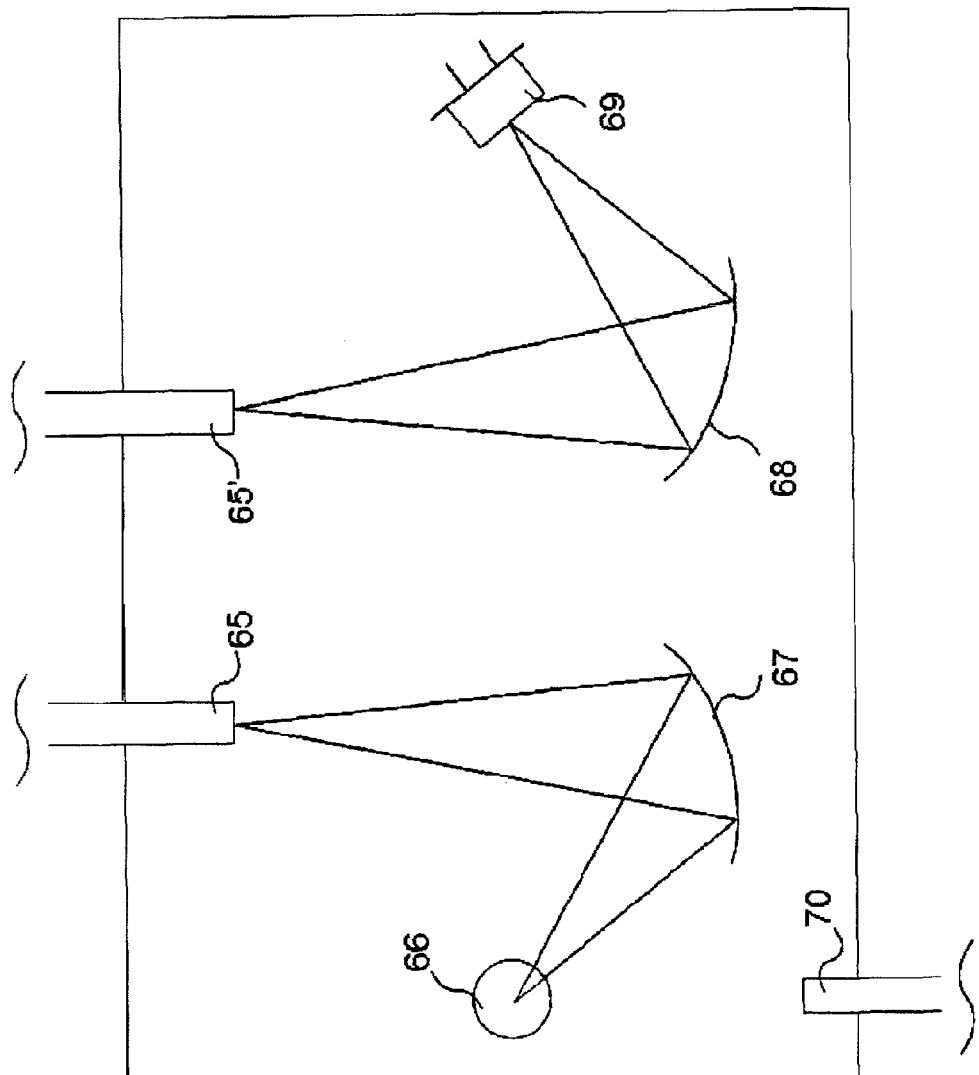
FIG. 10 is a diagram of a part of the optical system using hollow optical fibers.

Further, for example, hollow optical fibers may be used in the optical system while replacing air in an optical path inside the hollow optical fiber with nitrogen or argon. When the hollow optical fibers are used, the optical system can be divided into two portions on connection with the optical fibers, as shown in FIGS. 9 and 10. In an example shown in FIGS. 9 and 10, an ATR probe 61 is set to a wall face of a pipe for introducing a cleaning liquid. The ATR probe 61 is semispherical. Incident light 63 from a hollow optical fiber 65 (at the in-coming side) is incident on an interface of the ATR probe 61 with the cleaning liquid, and is reflected totally. The reflected light enters into the other hollow optical fiber 65' (at the out-going side). The optical fibers 65, 65' are arranged according to the incident angle of light. On the other hand, the other components in the optical systems are set in an air-tight structure (housing) shown in FIG. 10. Far ultraviolet light generated by a light source 66 is reflected by a grating 67 and enters into the optical fiber 65 at the in-coming side. Reflection light from the hollow optical fiber 65' is further reflected by a mirror 68 and is detected by an optical detector 69. Nitrogen gas which does not absorb light in the far ultraviolet range is introduced from an inlet 70 into the air-tight structure in order to purge oxygen gas and enters into the hollow portions in the optical fibers 65, 65'. Then, it goes out from the other ends thereof as shown in FIG. 9.

FIGS. 7 to 10 show the various structures of far ultraviolet measurement apparatuses. It is to be noted that components disclosed therein may be combined in various ways. For example, the hollow optical fibers shown in FIGS. 9 and 10 can also be used in the structures shown in FIGS. 7 and 8.

The invention claimed is:

1. A method for measuring total reflection light with a far ultraviolet attenuated total reflection probe, wherein penetration depth of evanescent waves of total reflection light is equal to or higher than 150 nm in far ultraviolet wavelength range, the penetration depth being dependent on wavelength of far ultraviolet light, refractive index of an object to be measured, refractive index of optical material of the probe and incident angle of the far ultraviolet light on an interface between the probe and the object, the method comprising:

providing the attenuated total reflection probe made of an optical material selected so as to have the penetration depth equal to or higher than 150 nm in far ultraviolet wavelength range, to make the probe contact with the object to be measured at an interface between the probe and the object;

making the far ultraviolet light incident on the interface, the light having a wavelength in the wavelength range and having incident angle larger than critical angle so as to have the penetration depth equal to or higher than 150 nm; and measuring the total reflection light from the interface, to determine absorbance of the object to be measured.

2. The method according to claim 1, wherein the optical material is synthetic quartz, the object to be measured is an aqueous solution, and the far ultraviolet wavelength range is between 170 and 175 nm.

3. The method according to claim 1, wherein the optical material is synthetic quartz, the object to be measured is an aqueous solution, and a wavelength in the wavelength range between 170 and 300 nm and the incident angle larger than critical angle are selected so as to have the penetration depth equal to or higher than 100 nm.

4. The method according to claim 1, wherein the aqueous solution is a cleaning liquid used in a semiconductor fabrication process, the method further comprising obtaining concentrations of components in the cleaning liquid from the absorbance.

5. An apparatus for measuring concentrations with attenuated total reflection far ultraviolet spectroscopy, comprising:

an attenuated total reflection probe made of synthetic quartz, fixed to and integrated with a wall made of synthetic quartz of a cleaning vessel for containing a cleaning liquid for a semiconductor;

a guiding optical system for guiding far ultraviolet light ray to an interface between the probe and the cleaning liquid at an incident angle larger than critical angle; and a receiving optical system for receiving total reflection light from the interface with an optical detector.

6. The apparatus according to claim 5, wherein each of the guiding optical system and the receiving optical system includes a hollow optical fiber, an end of the hollow optical fiber in the guiding optical system being arranged near an in-coming plane of the probe, an end of the hollow optical fiber in the receiving optical system being arranged near an out-going plane of the probe, air in the hollow optical fibers being replaced with a gas not absorbing the far ultraviolet light.

7. The apparatus according to claim 5, wherein the attenuated total reflection probe is made of an optical material having refractive index selected to have penetration depth of evanescent waves of total reflection light equal to or higher than 150 nm in far ultraviolet wavelength range, the penetration depth being determined by wavelength of the far ultraviolet light, refractive index of the object to be measured, the refractive index of optical material of the probe and incident angle of the far ultraviolet light entering the interface between the probe and the object.

8. An apparatus for measuring concentrations to be arranged beside a rotary stage on which a semiconductor is placed and to which a cleaning liquid for cleaning a semiconductor is ejected, comprising:
- an attenuated total reflection probe made of synthetic quartz, arranged at a position on which the cleaning liquid drops from the rotary stage;
- a guiding optical system for guiding far ultraviolet light ray to an interface between the probe and the cleaning liquid at an incident angle larger than critical angle; and
- a receiving optical system for receiving total reflection light from the interface of the probe with an optical detector.

9. The apparatus according to claim 8, wherein each of the guiding optical system and the receiving optical system includes a hollow optical fiber, an end of the hollow optical fiber in the guiding optical system being arranged near an in-coming plane of the probe, an end of the hollow optical fiber in the receiving optical system being arranged near an out-going plane of the probe, air in the hollow optical fibers being replaced with a gas not absorbing the far ultraviolet light.

10. The apparatus according to claim 8, wherein the attenuated total reflection probe is made of an optical material having refractive index selected to have penetration depth of evanescent waves of total reflection light equal to or higher than 150 nm in far ultraviolet wavelength range, the penetration depth being determined by wavelength of the far ultraviolet light, refractive index of the object to be measured, the refractive index of optical material of the probe and incident angle of the far ultraviolet light entering the interface between the probe and the object.

11. An apparatus for measuring concentrations to be integrated with a pipe through which a cleaning liquid for a semiconductor flows, the pipe being made of synthetic quartz, comprising:
- an attenuated total reflection probe made of synthetic quartz, arranged to provide an interface between the probe and the cleaning liquid at a position in contact with the cleaning liquid flowing through the pipe;
- a guiding optical system for guiding far ultraviolet light ray to an interface between the probe and the cleaning liquid at an incident angle larger than critical angle; and
- a receiving optical system for receiving total reflection light from the interface of the probe with an optical detector.

12. The apparatus according to claim 11, wherein each of the guiding optical system and the receiving optical system includes a hollow optical fiber, an end of the hollow optical fiber in the guiding optical system being arranged near an in-coming plane of the probe, an end of the hollow optical fiber in the receiving optical system being arranged near an out-going plane of the probe, air in the hollow optical fibers being replaced with a gas not absorbing the far ultraviolet light.

13. The apparatus according to claim 11, wherein the attenuated total reflection probe is made of an optical material having refractive index selected to have penetration depth of evanescent waves of total reflection light equal to or higher than 150 nm in far ultraviolet wavelength range, the penetration depth being determined by wavelength of the far ultraviolet light, refractive index of the object to be measured, the refractive index of optical material of the probe and incident angle of the far ultraviolet light entering the interface between the probe and the object.

\* \* \* \* \*